United States Patent
Petit et al.

(10) Patent No.: US 7,685,000 B1
(45) Date of Patent: Mar. 23, 2010

(54) PREDICTIVE MODELING SYSTEM AND METHOD FOR DISEASE MANAGEMENT

(75) Inventors: Parker H. Petit, Roswell, GA (US); Martin L. Olson, Marietta, GA (US)

(73) Assignee: Matria Healthcare, Inc., Marietta, GA (US)

( * ) Notice: Subject to any disclaimer, the term of this patent is extended or adjusted under 35 U.S.C. 154(b) by 1222 days.

(21) Appl. No.: 11/200,804

(22) Filed: Aug. 10, 2005

(51) Int. Cl.
- *G06Q 10/00* (2006.01)
- *G06Q 50/00* (2006.01)
- *G06Q 40/00* (2006.01)
- *A61B 5/00* (2006.01)
- *G06F 19/00* (2006.01)

(52) U.S. Cl. .................... 705/2; 705/3; 705/4
(58) Field of Classification Search .............. 705/2, 705/4; 5/3
See application file for complete search history.

(56) References Cited

U.S. PATENT DOCUMENTS

| | | | |
|---|---|---|---|
| 5,299,119 A | 3/1994 | Kraf et al. | |
| 5,301,105 A | 4/1994 | Cummings, Jr. | |
| 5,471,382 A | 11/1995 | Tallman et al. | |
| 5,550,734 A * | 8/1996 | Tarter et al. | 705/2 |
| 5,583,758 A | 12/1996 | McIlroy et al. | |
| 5,764,923 A | 6/1998 | Tallman et al. | |
| 5,827,180 A | 10/1998 | Goodman | |
| 5,915,386 A | 6/1999 | Lloyd et al. | |
| 5,953,704 A | 9/1999 | McIlroy et al. | |
| 5,957,867 A | 9/1999 | Lloyd et al. | |
| 5,964,700 A | 10/1999 | Tallman et al. | |
| 6,077,222 A | 6/2000 | Lloyd et al. | |
| 6,080,106 A | 6/2000 | Lloyd et al. | |
| 6,208,973 B1 * | 3/2001 | Boyer et al. | 705/2 |
| 6,234,964 B1 | 5/2001 | Iliff | |
| 6,409,662 B1 | 6/2002 | Lloyd et al. | |
| 6,484,144 B2 * | 11/2002 | Martin et al. | 705/2 |
| 2001/0020229 A1 | 9/2001 | Lash | |
| 2002/0049615 A1 | 4/2002 | Huber | |
| 2002/0099686 A1 | 7/2002 | Schwartz et al. | |
| 2002/0138304 A1 | 9/2002 | Fontanesi | |
| 2003/0036686 A1 | 2/2003 | Iliff | |
| 2003/0069755 A1 | 4/2003 | Abraham-Fuchs et al. | |
| 2003/0097279 A1 | 5/2003 | deLusignan et al. | |
| 2003/0153819 A1 | 8/2003 | Iliff | |
| 2004/0039600 A1 | 2/2004 | Kramer et al. | |
| 2005/0080462 A1 | 4/2005 | Jenkins et al. | |

OTHER PUBLICATIONS

More Choices for You in 2001; 4 pgs.
Summary of the Wellness Program for 2000; 6 pgs.
Winninghabits.com Service Agreement; May 30, 2001; 4 pgs.

* cited by examiner

*Primary Examiner*—Gerald J. O'Connor
*Assistant Examiner*—Amber L Altschul
(74) *Attorney, Agent, or Firm*—Gardner Groff Greenwald & Villanueva, PC

(57) ABSTRACT

A method and system for administering a disease management program to improve healthcare quality, reduce healthcare costs, and optimize delivery of healthcare services. A multi-condition risk assessment is conducted for all or a substantial portion of a population of program participants, and collected multi-condition risk assessment data are combined with claims data for predictive modeling of future healthcare risk and expense. Participants are risk-stratified into one or more classifications of future healthcare cost risk, and appropriate intervention or delivery of healthcare services is made based on the risk classification.

17 Claims, 1 Drawing Sheet

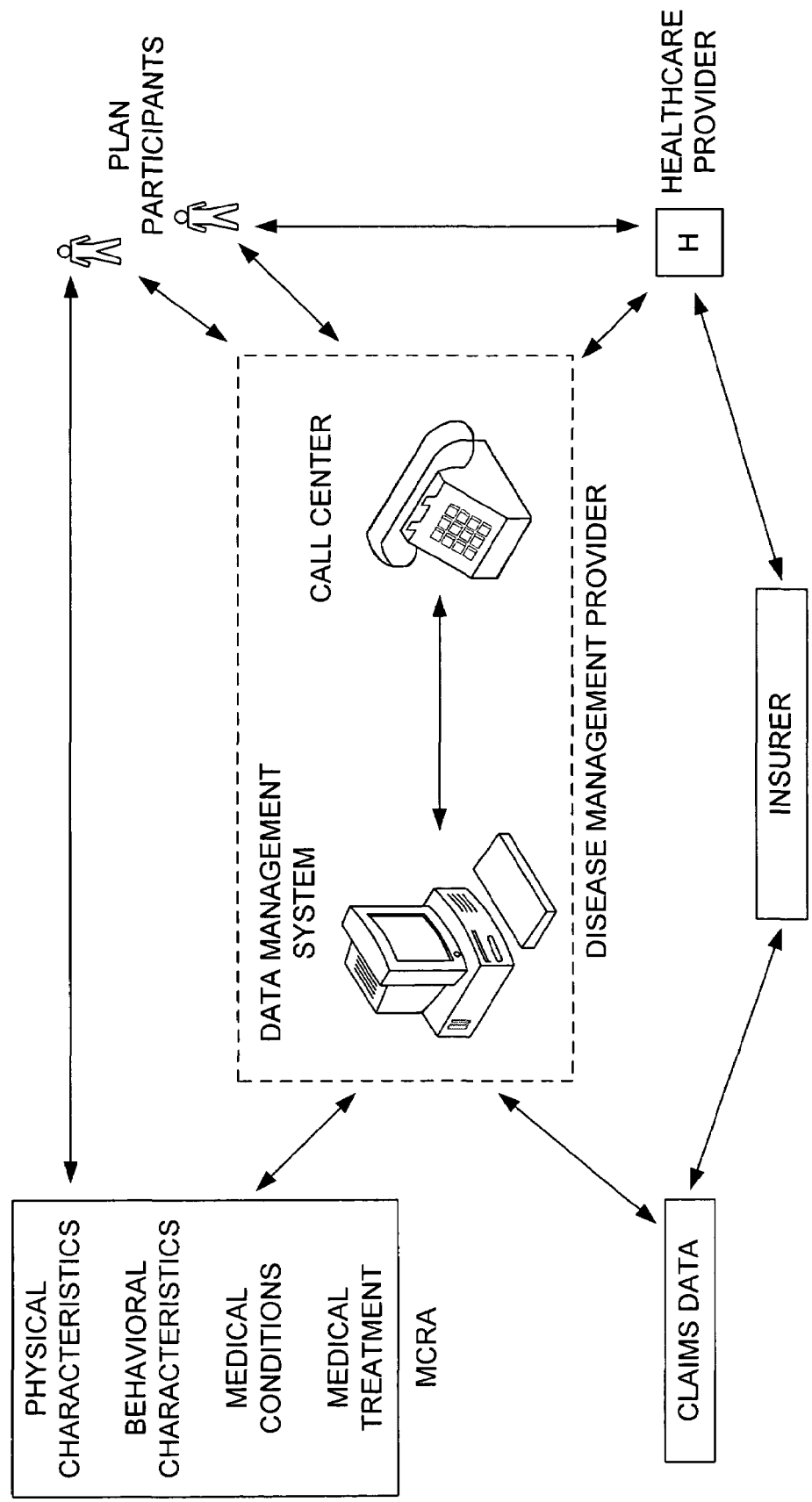

PREDICTIVE MODELING SYSTEM AND METHOD FOR DISEASE MANAGEMENT

TECHNICAL FIELD

The present invention relates generally to the field of disease management, and more particularly to a system and method of identification, validation and risk stratification utilizing predictive modeling in combination with a multi-condition risk assessment tool.

BACKGROUND OF THE INVENTION

Disease management is an approach to patient care and medical cost control that is based on the premise that a minority of healthcare users generate the majority of total healthcare costs. Disease management programs use information technology to identify individuals who have or are at risk for various adverse medical conditions. Disease management programs offer customized education and clinical support to help individuals take more responsibility for self-care, improve their health, and avoid expensive medical events down the road. By proactively improving the health of the minority of a population that consumes the majority of healthcare resources, disease management programs can significantly reduce many preventable medical expenses, including hospitalization and ER visits.

Disease management programs commonly segment an overall population of healthcare consumers within a program into multiple risk categories, and provide varying levels of monitoring and care to individual program participants depending on their risk categorization. This is variously termed "risk stratification" or "predictive modeling." Preemptive interventions triggered by a high-risk stratification will, on average, increase the quality of care, reduce adverse clinical events, and accordingly reduce paid claims dollars. To distinguish high-risk persons from low-risk persons, traditional identification and predictive modeling programs have typically utilized a retrospective claims analysis method that partitions the population based on prior medical utilization or historical health plan claims data, and then sets care levels appropriately.

Predictive modeling based solely on retrospective claims data is of limited accuracy in estimating future risk, however, and therefore needs exist for continued improvement in the field of disease management identification and risk stratification. It is to the provision of improved systems and methods of disease management that the present invention is primarily directed.

SUMMARY OF THE INVENTION

The present invention provides improved systems and methods of identification and risk stratification for disease management. In example forms, the present invention incorporates a multi-condition risk assessment to collect data elements from all or a substantial portion of program participants within an identified population. The collected multi-condition risk assessment data is then combined with analysis of medical claims data, resulting in substantially improved accuracy in estimating future risk, and more effective targeting of education, clinical support, and intervention resources within a disease management program. In this manner, a more efficient allocation of resources may be realized, to provide better and more efficient patient care and greater cost reductions than typical programs.

In one aspect, the present invention is a method of disease management, preferably including the steps of defining a population of program participants based on claims data filtering, conducting a multi-condition risk assessment of all or substantially all program participants in the defined population, combining data gathered from that multi-condition risk assessment with claims data for each program participant in the defined population, and classifying future healthcare risk of the program participants based on the combination of claims data and data gathered from the multi-condition risk assessment.

In another aspect, the invention is a method of disease management, preferably including the steps of conducting a multi-condition risk assessment of each program participant within a defined population, generating a patient record for each program participant in the population, and providing differing degrees of healthcare intervention for program participants based on their patient record.

In still another aspect, the invention is a method of optimizing delivery of healthcare services to participants in a disease management program. The method preferably includes conducting a multi-condition risk assessment of at least a substantial portion of a defined population, categorizing individual program participants selected from the population into at least a higher-risk category and a lower-risk category, and providing more intensive healthcare intervention to program participants categorized in the higher-risk category and less intensive healthcare intervention to program participants categorized in the lower-risk category.

These and other aspects, features and advantages of the invention will be understood with reference to the detailed description herein, and will be realized by means of the various elements and combinations particularly pointed out in the appended claims. It is to be understood that both the foregoing general description and the following detailed description of the invention are exemplary and explanatory of preferred embodiments of the invention, and are not restrictive of the invention, as claimed.

BRIEF DESCRIPTION OF THE DRAWING FIGURE

The drawing FIGURE shows schematically a system and method of disease management incorporating a multi-condition risk assessment, according to an example form of the present invention.

DETAILED DESCRIPTION OF EXAMPLE EMBODIMENTS

The present invention may be understood more readily by reference to the following detailed description of the invention. It is to be understood that this invention is not limited to the specific devices, methods, conditions or parameters described herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Preferred and example forms of the disease management system and method of the present invention improve upon the effectiveness of previously known systems and methods by combining predictive modeling based on retrospective claims data with information gathered from a multi-condition risk assessment ("MCRA") of program participants within a defined population. For example, one or more of the following data elements is/are typically extracted from retrospective claims data for patients participating in a disease management plan: (1) date that a healthcare service was performed; (2) place the service was performed; (3) type of service that was performed; (4) medical diagnoses; (5) the occurrence of lab testing, and/or lab test results; (6) procedures carried out; (7) medical codes for services performed; (8) pharmacy prescriptions and codes; (9) amount the insurance carrier paid; (10) type of provider that performed the service (e.g., cardiologist, emergency room physician, etc.); and/or (11) dates of admission and discharge for inpatient claims.

Because such data is gathered from prior claims, predictive modeling is typically based on data collected from those program participants who have received medical attention resulting in an insurance claim, and participants not incurring claims typically do not contribute data used for predictive modeling under previously known systems and methods of disease management. Accordingly, previously known predictive modeling processes may help identify program participants with chronic conditions that have required some level of medical care in the past and are more likely to generate high medical costs for related conditions in the future, but such a predictive modeling process alone typically cannot identify higher-risk participants who have not yet sought treatment and incurred claims, nor does it optimally reflect risk for others whose claims underestimate disease burden (such as participants who have been non-compliant with prescribed treatment programs and therefore have not incurred claims that they should have, or have incurred fewer claims than they should have).

By conducting a multi-condition risk assessment of program participants within a defined population, and combining data gathered from the multi-condition risk assessment with predictive modeling and other data, the system and method of the present invention is better able to predict which participants would most benefit from some form of preemptive healthcare intervention, and more efficiently deliver appropriate forms and degrees of healthcare intervention. The drawing FIGURE shows an example system and method according to the present invention. Preferably, participants in a disease management program are screened using one or more claims data filters to identify a defined population or subgroup of program participants. For example, claims data filter mechanisms according to the present invention may identify program participants whose claims data indicate potential risk for a disease or condition to be monitored (e.g., diabetes, coronary artery disease, congestive heart failure, chronic obstructive pulmonary disease, asthma), a specified level or frequency of claims, and/or other potential indicator of increased risk of future uncommon medical expense. Additionally or alternatively, the defined population or subgroup of program participants may include self-referred and/or physician-referred program participants having indications of one or more identified conditions or risks. In alternate embodiments of the invention, all participants in a disease management program are included in the defined population.

A multi-condition risk assessment is then conducted according to the present invention for all or a substantial portion of the defined population of program participants. The multi-condition risk assessment is preferably carried out independently of any retrospective data collection based on prior healthcare claims. In this manner, data elements are collected as part of the multi-condition risk assessment, even for those program participants not yet having incurred claims, or whose retrospective claims data alone would not indicate a higher risk of increased healthcare needs in the near or longer-term future. In example forms of the invention, a preliminary multi-condition risk assessment is conducted for participants upon their entry into a disease management program. Alternatively or additionally, multi-condition risk assessments are conducted for existing participants, for example on a periodic basis, upon occurrence of a specified event (e.g., a birthday or other age-based event, after a set number of months in the program, etc.), upon random selection, at the convenience of the individual participant, and/or on some other basis. The multi-condition risk assessment may be carried out via an Internet-based online question-and-answer session, by telephone questionnaire, in-person interview, or by filling out a paper questionnaire. The multi-condition risk assessment may collect information directly from the participant, or from the participant's designee (e.g., a parent, guardian or caregiver).

The multi-condition risk assessment preferably includes collection of data including one or more medical factors or conditions of an individual program participant, such as blood pressure (hypertension), cholesterol levels, diabetes, elevated blood-glucose levels, swelling or inflammation, chest pain, fatigue, shortness of breath, depression, cancer, low back pain, cardiac disease (congestive heart failure, coronary artery disease), and/or respiratory disease (asthma, chronic obstructive pulmonary disease). The multi-condition risk assessment preferably also includes collection of data relating to one or more medical treatments of an individual program participant, such as prescription or non-prescription drugs taken, insulin therapy, oxygen therapy, and/or compliance with prescribed treatment regimens.

Preferably, data collected from the multi-condition risk assessments of individual program participants are combined with retrospective claims data and/or other information to develop a patient record or clinical profile for each program participant within the defined population. Preferably, the records are updated continuously or periodically, as for example with automated claims data feeds, and/or supplemental multi-condition risk assessment data. Preferably, a combination of data from the multi-condition risk assessments and claims data is applied to a statistical model to stratify risk and classify individual participants within the defined population into one of two or more risk classifications. For example, the combination of data may be utilized for individual health risk identification purposes such as identification of undiagnosed conditions and future health risks, monitoring for statistically predicted co-morbidities and potential complications, and/or other means of categorization of future healthcare cost risk severity. Preferably, patient record data are also utilized for determining the appropriate level of disease management intervention and support for individual program participants. Preferably, the degree or intensity of recommended intervention or support increases with increasing risk severity classification, for example ranging from patient education for lesser risk individuals, through passive monitoring and reporting of progress and program compliance for medium risk individuals, to more active intervention and close one-on-one case management for higher risk individuals.

Preferably, the patient record data for all program participants are also aggregated for program analysis and reporting purposes, such as reporting utilization levels, cost savings performance, population statistics, financial indicators, etc. The aggregated data from patient records are optionally analyzed periodically or continuously to provide statistical feedback on the risk assessment and outcome predictive models utilized by the program, and to adjust and optimize those models over time based on actual program results.

In preferred and example forms, the system and method of the present invention are implemented using a computer based data-management and services-delivery system, and associated computer software as stored in system memory and/or on computer-readable media. In particular embodiments, two or more computers within the data management system communicate data over a global communications network such as the Internet. In this manner, the program provider optionally provides automated data management, scheduling, monitoring, and healthcare education and intervention delivery services through online and/or call-center communication systems. For example, preferably, the computer based system and method of the present invention receive input data including retrospective claims data and information gathered from a multi-condition risk assessment of program participants. The received data are stored and processed to generate a patient record or clinical profile for each program participant in a defined population. Optionally, the profile and/or underlying data are reported to and/or remotely accessed by the participant and/or the participant's doctor or other healthcare provider(s) through secure communications links. The profile and/or underlying data are processed to identify undiagnosed medical conditions, monitor previously identified conditions, and/or classify future medical risk level.

Based upon the determined risk classification, identified conditions, and/or other information from their profile, the participant may be contacted with customized information regarding proposed treatment, monitoring, recommended lifestyle or behavior changes, and/or other risk-mitigation steps, based on clinically accepted practices. Optionally, automated reminders and/or proactive monitoring of conditions, progress and/or program compliance are generated, and are communicated to the participant by email, telephonically by call-center personnel, or otherwise. Preferably, the frequency and content of these contacts are customized by the system based on each participant's individual profile or risk classification, including severity of condition, and the participant's degree of cooperation and compliance. Automated scheduling and reminders of doctor visits, testing and monitoring, medication delivery and usage, and other activities are optionally provided to the program participant.

Optionally, the program also provides on-demand counseling and help-line services, preferably staffed with specialized healthcare professionals who can access the participant's profile, and query and advise the participant based on system generated information specific to the participant. The healthcare professionals may also be prompted to proactively initiate a contact with the participant, for example to monitor progress or direct program compliance, and/or to support or advise the participant with respect to particular aspects of their care.

While the invention has been described with reference to preferred and example embodiments, it will be understood by those skilled in the art that a variety of modifications, additions and deletions are within the scope of the invention, as defined by the following claims.

What is claimed is:

1. A method of disease management embodied in a computer program product for execution on an instruction processing system, comprising a tangible storage medium readable by the instruction processing system and storing instructions for execution by the instruction processing system for performing the method comprising:
    filtering claims data of program participants to define a population;
    conducting a multi-condition risk assessment of substantially all participants within the defined population;
    combining data gathered from said multi-condition risk assessment with claims data for participants within the defined population;
    classifying future healthcare risk of participants based on the combination of claims data and data gathered from said multi-condition risk assessment; and
    determining an appropriate level of disease management intervention and support for program participants based on the future healthcare risk classification that ranges from patient education for lower risk individuals, passive monitoring and reporting of progress and program compliance for middle risk individuals, to more active intervention and close one-on-one case management for higher risk individuals.

2. The method of claim 1, further comprising directing a plan of care based on the classification of future healthcare risk.

3. The method of claim 1, wherein the step of conducting a multi-condition risk assessment comprises gathering data regarding one or more medical conditions of the program participant.

4. The method of claim 3, wherein the data regarding one or more medical conditions of the program participant are selected from blood pressure, hypertension, cholesterol levels, diabetes, elevated blood-glucose levels, swelling or inflammation, chest pain, fatigue, shortness of breath, depression, cancer, low back pain, cardiac disease, congestive heart failure, coronary artery disease, respiratory disease, asthma, chronic obstructive pulmonary disease, and combinations thereof.

5. The method of claim 1, wherein the step of conducting a multi-condition risk assessment comprises gathering data regarding one or more medical treatments of the program participant.

6. The method of claim 5, wherein the data regarding one or more medical treatments of the program participant are selected from prescription or non-prescription drugs taken, insulin therapy, oxygen therapy, compliance with prescribed treatment regimens, and combinations thereof.

7. The method of claim 1, wherein a multi-condition risk assessment is conducted for every member of the defined population of program participants.

8. The method of claim 1, wherein the multi-condition risk assessment is a preliminary multi-condition risk assessment conducted upon entry of the participant into a disease management program.

9. The method of claim 1, wherein the multi-condition risk assessment is conducted upon occurrence of a specified event.

10. The method of claim 1, wherein the multi-condition risk assessment is conducted via an Internet-based online question-and-answer session.

11. The method of claim 1, wherein the step of filtering claims data of program participants comprises identification of at least one potential indicator of increased risk of future uncommon medical expense.

12. The method of claim 1, wherein the combination of data from the multi-condition risk assessment and claims data is applied to a statistical model to stratify risk and classify individual participants within the defined population into one of two or more risk classifications.

13. The method of claim 1, wherein the defined population further comprises self-referred and/or physician-referred program participants having indications of one or more identified conditions or risks.

14. A method of disease management embodied in a computer program product for execution on an instruction processing system, comprising a tangible storage medium readable by the instruction processing system and storing instructions for execution by the instruction processing system for performing the method comprising:

conducting a multi-condition risk assessment of at least a substantial portion of program participants within a defined population;

generating a patient record based on the multi-condition risk assessment; and providing differing degrees of healthcare intervention for program participants based on their patient record, wherein the degrees range from patient education for lower risk individuals, passive monitoring and reporting of progress and program compliance for middle risk individuals, to more active intervention and close one-on-one case management for higher risk individuals.

15. The method of claim 14, further comprising collecting retrospective claims data for program participants, and combining said retrospective claims data into the patient records.

16. A method of optimizing delivery of healthcare services to participants in a disease management program, embodied in a computer program product for execution on an instruction processing system, comprising a tangible storage medium readable by the instruction processing system and storing instructions for execution by the instruction processing system for performing said method comprising:

conducting a multi-condition risk assessment of at least a substantial portion of a population;

categorizing individual program participants selected from the population into at least a higher-risk category and a lower-risk category; and providing more intensive healthcare intervention to program participants categorized in the higher-risk category and less intensive healthcare intervention to program participants categorized in the lower-risk category, wherein the program participants categorized in the lower-risk category receive patient education and close one-on-one case management for higher-risk category.

17. The method of claim 16, further comprising collecting claims data for program participants, and wherein the step of categorizing individual program participants selected from the population into at least a higher-risk category and a lower-risk category comprises combining said claims data with data collected by the multi-condition risk assessment.

* * * * *